United States Patent [19]

Cobb

[11] Patent Number: 4,556,750

[45] Date of Patent: Dec. 3, 1985

[54] ALKYLATION PROCESS

[75] Inventor: R. Lynn Cobb, Bartlesville, Okla.

[73] Assignee: Phillips Petroleum Company, Bartlesville, Okla.

[21] Appl. No.: 722,625

[22] Filed: Apr. 12, 1985

Related U.S. Application Data

[63] Continuation of Ser. No. 385,248, Jun. 4, 1982, abandoned.

[51] Int. Cl.⁴ .............................................. C07C 2/66
[52] U.S. Cl. .................................. 585/446; 585/449; 585/465; 585/467
[58] Field of Search ............... 585/446, 449, 462, 463, 585/465, 467

[56] References Cited

U.S. PATENT DOCUMENTS

| | | | |
|---|---|---|---|
| 2,308,786 | 1/1943 | Smith | 585/446 |
| 2,400,437 | 5/1946 | Perkins et al. | 585/449 |
| 2,584,103 | 2/1952 | Pines et al. | 585/463 |
| 2,768,985 | 10/1956 | Schlatter | 585/321 |
| 2,819,323 | 1/1958 | McCaulay | 585/473 |
| 3,118,956 | 1/1964 | Feighner et al. | 585/449 |
| 3,207,800 | 5/1962 | Williamson et al. | 585/449 |
| 3,849,507 | 11/1974 | Zuech | 585/455 |
| 4,225,737 | 9/1980 | Mikulicz et al. | 585/449 |

Primary Examiner—William R. Dixon, Jr.
Assistant Examiner—Cynthia A. Prezlock
Attorney, Agent, or Firm—S. E. Reiter

[57] ABSTRACT

In an alkylation process a portion of the alkylating olefin is added to benzene before heating the benzene up to the alkylation reaction temperature.

7 Claims, No Drawings

ALKYLATION PROCESS

This application is a continuation of application Ser. No. 385,248, filed June 4, 1982, now abandoned.

My invention relates to an improved method for the alkylation of benzene. Another aspect of my invention relates to a method for increasing the yield of dialkyl substituted benzene compounds.

The prior art process for the synthesis of dialkyl substituted benzene compounds, of which my invention is an improvement, comprises (1) adding an alkylation catalyst to benzene to form a mixture; (2) heating the mixture at a suitable alkylation temperature; and (3) adding to the heated mixture an alkylating olefin suitable to produce dialkyl substituted benzene compounds.

I have found that by adding a portion of the alkylating olefin to the benzene-catalyst mixture prior to the heat-up period the yield of dialkyl substituted benzene compounds can be increased. In a specific embodiment I have found that the yield of 1,4-ditertiary-alkylbenzene can be increased.

Dialkyl benzenes can be used to produce surfactants by reaction with $H_2SO_4$, preferably $SO_3$, or more preferably $SO_3$ dissolved in $SO_2$ to produce the corresponding sulfonic acids which in turn are neutralized with a base such as sodium hydroxide to produce the corresponding salts. Numerous uses for such surfactants are well known in the art and include, for example, enhanced oil recovery. Dialkyl benzenes can also be used as fuels in combustion operations.

1,4-ditertiary-alkylbenzenes have a variety of uses which include, for example, the use of p-ditertiary-butylbenzene as an intermediate in the fragrance industry, in synthesizing a surfactant (1-t-butyl-4-t-butyldisulfonylchlorobenzene) and as a textile assistant (see U.S. Pat. No. 3,470,246). Other examples include 1,4-dipropylbenzene (p-propyl-propylbenzene) useful as a scavenger for alkyl lead antiknock agents and as a pesticide (see U.S. Pat. No. 3,787,512); and 1,4-didodecylbenzene useful as an ingredient in an electrical insulation composition (see Chemical Abstracts, Vol. 63:18461a).

It is an object of this invention to increase the yield of dialkyl substituted benzene compounds in an alkylation process.

It is another object of this invention to increase the yield of 1,4-ditertiary-alkylbenzene in an alkylation process.

These objects and other objects and advantages of my invention will become apparent from this disclosure and the appended claims.

My invention is a process for increasing the yield of dialkyl substituted benzene by adding a portion of an alkylating olefin to benzene and an alkylation catalyst before heating the benzene-catalyst mixture. My benzene alkylation process can be described as follows:

(1) Adding together benzene, an alkylating catalyst and an alkylating olefin.

(2) Heating the mixture in (1) to a suitable alkylation temperature.

(3) Adding additional alkylating olefin to the heated mixture.

For purposes of nomenclature step (2) is referred to herein as the heat-up period.

As compared to the prior art process, wherein a portion of the alkylating olefin is not added to benzene prior to the heat-up period, my process yields an increased amount of dialkyl substituted benzene. In an embodiment of my invention my process yields an increased amount of 1,4-ditertiary-alkylbenzene such as, for example, 1,4-ditertiary-butylbenzene.

The alkylating olefins useful in the practice of this invention can be represented by the following formula:

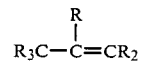

wherein each R independently represents a hydrogen atom or an alkyl radical having from 1 to about 9 carbon atoms. It is preferred that the total number of carbon atoms not exceed 12. Suitable olefins include, but are not limited to, the following:

propylene
isobutylene
1-butene
1-pentene
1-hexene
2-hexene
3-hexene
3-methyl-1-hexene
1-octene
1-decene
1-dodecene
2-dodecene.

Mixtures of any of the above-defined alkylating olefins are also contemplated to be within the scope of my invention. In other words the alkylating olefin in steps (1) and/or (3) above can be a mixture of two or more of the above-defined olefins.

Although my invention is not limited to any particular range the amount of alkylating olefin added to the benzene before the heat-up period preferably ranges from about 10 to about 50 percent and more preferably from about 15 to about 35 percent, based on the total amount of alkylating olefin used in the alkylation process. The optimum percentage of olefin added before the heat-up period will depend upon variables such as the specific olefin and catalyst used, reaction conditions, etc.

The type of catalyst used in the practice of my invention is not considered to be critical. The novelty of my process lies in the addition of a portion of the alkylating olefin to the benzene prior to the heat-up period. Any catalyst useful in the alkylation of benzene with the previously defined alkylating olefins is considered to be within the scope of my invention. Suitable catalysts include, but are not limited to, the following:

acid-treated montmorillonite (Filtrols)
boron trifluoride
boron trifluoride: phosphoric acid complex
boron trifluoride: etherate Inert solvents can be used as desired to facilitate the practice of my invention. Suitable inert solvents include, but are not limited to, heptane and hexane.

Although the scope of my invention is not limited to specific reaction conditions the following reaction temperature and pressure ranges are disclosed to aid others in practicing the invention.

|  | Broad | Preferred |
| --- | --- | --- |
| Temperature, °C. | 50–250 | 130–190 |
| Pressure, atms | 0–500 | 0–100 |

The following examples are given to illustrate the practice of my invention and should not be interpreted to unduly limit its scope.

EXAMPLE I

This is a control example that illustrates the prior art procedure for synthesizing dialkyl substituted benzene compounds such as 1,4-ditertiary-butylbenzene. This example demonstrates the lower yield obtained when all of the alkylating olefin is added to the benzene at the reaction temperature after the heat-up period. The procedure was as follows: 375 milliliters (4.23 moles) of benzene and 25 milliliters of catalyst Filtrol 13 LVM (low volatile matter) (Filtrol Corp., Los Angeles, California) were added to a 1-liter stainless steel stirred autoclave. After the reactor was sealed the contents were stirred and heated. Stirring and heating continued until the temperature reached about 170° C. at which point isobutylene was added at a rate of 1 milliliter per minute until a total of 124 grams (2.21 moles) of isobutylene had been added. The temperature was maintained between 170° C. and 185° C. After all of the isobutylene had been added, the mixture was stirred for a few minutes and cooled to about 25° C. A sample of the reactor effluent was analyzed by gas liquid chromatography (GLC) using as a column 5% SP1200 (low polarity ester-type stationary phase) and 1.75% Betone 34 (dimethyl dioctadecyl ammonium bentonite) on Supelcoport (acid-washed DMCS diatomite support from Supelco Inc., Bellfronte, Pennsylvania) at 40° to 200° C. at 10°/min increase. Analyses indicated a 47.8% benzene conversion with a product selectivity of 66% t-butylbenzene, 13% 1,3-di-t-butylbenzene and 20% 1,4-ditertiary-butylbenzene.

EXAMPLE II

This example illustrates my invention and demonstrates that a higher yield of 1,4-ditertiary-butylbenzene is obtained when a portion of the alkylating olefin is present in the reaction mixture before heat-up begins. The procedure was as follows: 375 milliliters (4.23 moles) of benzene and 25 milliliters of catalyst Filtrol 13 LVM (low volatile matter) were added to a 1-liter stainless steel stirred autoclave. After sealing the reactor 65 milliliters (38 grams, 0.678 moles) of isobutylene were added. Stirring was started and the contents were heated to 170° C., at which point more isobutylene was added at a rate of 1 milliliter per minute until a total of 144 grams (2.57 moles) of isobutylene had been added. The temperature was maintained between 170° C. and 185° C. After cooling, the reactor effluent was analyzed by gas liquid chromatography (GLC) as described in Example I. The results are listed in Table I along with the results of Example I for comparison.

The data show that the pre-heatup olefin addition strategy of my invention decreased the % product selectivity of TBB and increased the % product selectivity of 1,4-DTBB. The data further show that the pre-heatup addition of olefin did not significantly reduce the % conversion of benzene. Accordingly, the % product selectivity gives an approximate indication of the relative yield of each product. Therefore, the data indicate not only an increase in the yield of 1,4-DTBB but also an increase in the total yield of dialkyl substituted benzene compounds (i.e., 1,3-DTBB plus 1,4-DTBB). The decrease in 1,3-DTBB was more than offset by the gain in 1,4-DTBB.

Reasonable variations from and modifications of my invention as disclosed herein are contemplated to be within the scope of patent protection desired and sought. The essence of my invention resides in the addition of a portion of the alkylating olefin to benzene before heating the benzene up to the alkylation reaction temperature.

I claim:

1. A process for the dialkylation of benzene with isobutylene which comprises:
    (a) adding to said benzene and an alkylation catalyst about 10 to about 50 volume percent of the total amount of isobutylene to be used in the alkylation process;
    (b) heating the mixture produced in step (a) up to an alkylation reaction temperature; and
    (c) adding the remainder of the isobutylene to be used in the alkylation process to said heated mixture to produce ditertiary-butylbenzene.

2. A process in accordance with claim 1 wherein about 15 to about 35 volume percent of the total amount of isobutylene to be used in the alkylation process is added to said benzene and said alkylation catalyst in step (a).

3. A process in accordance with claim 1 wherein said alkylation reaction temperature is in the range of about 50° C.–250° C.

4. A process in accordance with claim 3 wherein said alkylation reaction temperature is in the range of about 130° C.–190° C.

5. A process in accordance with claim 3 wherein said alkylation catalyst is selected from the group consisting of:
    acid-treated montmorillonite,
    boron trifluoride,
    boron trifluoride: phosphoric acid complex, and
    boron trifluoride: etherate.

6. A process in accordance with claim 4 wherein said alkylation catalyst is acid-treated montmorillonite.

7. A process in accordance with claim 4 wherein 1,4-ditertiary-butylbenzene is produced.

* * * * *

TABLE I

| Process | % Benzene Conv. | % Product Selectivity by GLC | | |
|---|---|---|---|---|
| | | TBB[a] | 1,3-DTBB[b] | 1,4-DTBB[c] |
| Control - Example I | | | | |
| 1. 100 Vol. % isobutylene added after heat-up. | 47.8 | 66.1 | 13.2 | 19.2 |
| Invention - Example II | | | | |
| 2. 26 Vol. % isobutylene added before heat-up, 74 Vol. % isobutylene added after heat-up. | 47.1 | 47.1 | 8.0 | 36.5 |

[a]TBB = tertiary-butylbenzene
[b]1,3-DTBB = 1,3-ditertiary-butylbenzene
[c]1,4-DTBB = 1,4-ditertiary-butylbenzene

UNITED STATES PATENT AND TRADEMARK OFFICE
CERTIFICATE OF CORRECTION

PATENT NO. : 4,556,750

DATED : December 3, 1985

INVENTOR(S) : R. Lynn Cobb

It is certified that error appears in the above-identified patent and that said Letters Patent is hereby corrected as shown below:

Claim 5, line 6, please delete "trifluoride: phosphoric" and insert ---trifluoride·phosphoric---.

Claim 5, line 7, please delete "trifluoride: etherate." and insert ---trifluoride·etherate.---.

Signed and Sealed this

Third Day of June 1986

[SEAL]

Attest:

DONALD J. QUIGG

Attesting Officer

Commissioner of Patents and Trademarks